(12) United States Patent
Aarts et al.

(10) Patent No.: US 11,259,709 B2
(45) Date of Patent: Mar. 1, 2022

(54) APPARATUS FOR MEASURING A PHYSIOLOGICAL PARAMETER USING A WEARABLE SENSOR

(71) Applicant: KONINKLIJKE PHILIPS N.V., Eindhoven (NL)

(72) Inventors: Ronaldus Maria Aarts, Eindhoven (NL); Laurentia Johanna Huijbregts, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 218 days.

(21) Appl. No.: 16/038,323

(22) Filed: Jul. 18, 2018

(65) Prior Publication Data
US 2019/0021614 A1  Jan. 24, 2019

(30) Foreign Application Priority Data
Jul. 21, 2017  (EP) .................... 17182508

(51) Int. Cl.
*A61B 5/00* (2006.01)
*A61B 5/024* (2006.01)
*A61B 5/06* (2006.01)

(52) U.S. Cl.
CPC ...... *A61B 5/02405* (2013.01); *A61B 5/02416* (2013.01); *A61B 5/02438* (2013.01); *A61B 5/067* (2013.01); *A61B 5/068* (2013.01); *A61B 5/681* (2013.01); *A61B 5/6824* (2013.01); *A61B 5/6826* (2013.01); *A61B 5/6831* (2013.01); *A61B 2562/0204* (2013.01); *A61B 2562/0214* (2013.01); *A61B 2562/0219* (2013.01)

(58) Field of Classification Search
None
See application file for complete search history.

(56) References Cited

U.S. PATENT DOCUMENTS

| 5,406,952 | A  | 4/1995  | Barnes et al. |
| 6,491,647 | B1 | 12/2002 | Bridger |
| 8,926,509 | B2 | 1/2015  | Magar |

(Continued)

FOREIGN PATENT DOCUMENTS

| JP | 2004041482 A | 2/2004 |
| JP | 2016097237 A | 5/2016 |

(Continued)

OTHER PUBLICATIONS

"Biowatch: Estimation of heart and breathing rates from wrist motions", J. Hernandez, D. McDuff, R.W. Picard, 9th International Conference on Pervasive Computing Technologies for Healthcare (PervasiveHealth) 2015, pp. 169-176.

(Continued)

*Primary Examiner* — Erica S Lee

(57) ABSTRACT

A wearable physiological sensor has a housing and a gas-permeable support structure carried by the housing, which contacts the skin of the subject. An air space is provided between the support structure and the housing. Movement of the support structure relative to the housing is sensed. This provides a sensor which is comfortable for the subject and provides good sensitivity in that motion being detected (e.g. an arterial pulse) only needs to impart kinetic energy to the support structure, with a relatively low inertia.

12 Claims, 3 Drawing Sheets

(56) References Cited

U.S. PATENT DOCUMENTS

| | | |
|---|---|---|
| 9,351,685 B2 | 5/2016 | O'Neil |
| 9,439,599 B2 | 9/2016 | Thompson |
| 9,833,171 B2 | 12/2017 | Yin |
| 2007/0287923 A1 | 12/2007 | Adkins |
| 2008/0091090 A1 | 4/2008 | Guillory |
| 2008/0249393 A1 | 10/2008 | Finarov |
| 2014/0275832 A1 | 9/2014 | Muehlsteff |
| 2014/0278139 A1* | 9/2014 | Hong .................. A61B 5/1123 702/19 |
| 2014/0296734 A1* | 10/2014 | Tu ..................... A61B 5/02438 600/547 |
| 2016/0128626 A1* | 5/2016 | Johnson ................ A61B 5/681 600/301 |
| 2017/0042485 A1* | 2/2017 | Chung ................ A61B 5/7285 |
| 2017/0086519 A1* | 3/2017 | Vigano' ................ A61B 5/026 |
| 2017/0105899 A1* | 4/2017 | Joshi .................. A61H 31/004 |
| 2017/0143246 A1 | 5/2017 | Flickinger |
| 2017/0164850 A1 | 6/2017 | Murphy |
| 2017/0311849 A1* | 11/2017 | Lynde ................. A61B 5/1126 |
| 2017/0312515 A1* | 11/2017 | Ferree .................. A61B 5/4815 |
| 2017/0348156 A1* | 12/2017 | Duesterhoft ......... A61B 5/6831 |
| 2018/0028080 A1 | 2/2018 | Ouwerkerk |
| 2018/0116534 A1* | 5/2018 | Tal ........................ A61B 5/681 |
| 2018/0116571 A1 | 5/2018 | Ajima |
| 2018/0146870 A1* | 5/2018 | Shemesh ............ A61B 5/02438 |
| 2018/0146871 A1 | 5/2018 | Ajima |

FOREIGN PATENT DOCUMENTS

| | | |
|---|---|---|
| WO | 9417728 A1 | 8/1994 |
| WO | 2010104952 A2 | 9/2010 |
| WO | 2016175052 A1 | 11/2016 |

OTHER PUBLICATIONS

J. Hernandez, D. McDuff, R.W. Picard, Biowatch: Estimation of Heart and Breathing Rates From Wrist Motions, 9th International Conf. on Pervasive Computing Technologies for Healthcare, 2015.

\* cited by examiner

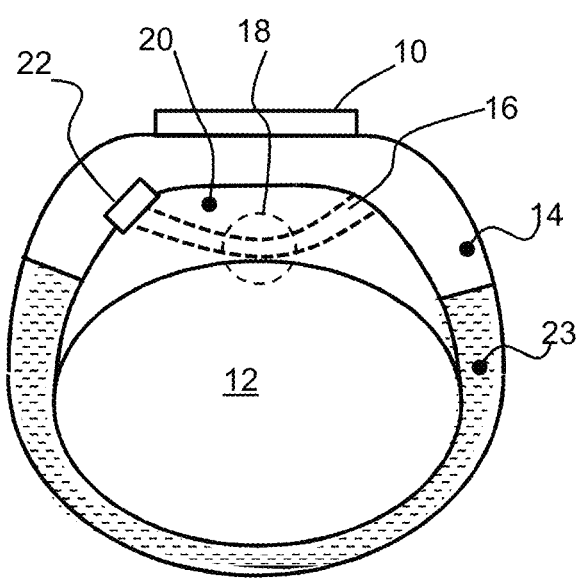
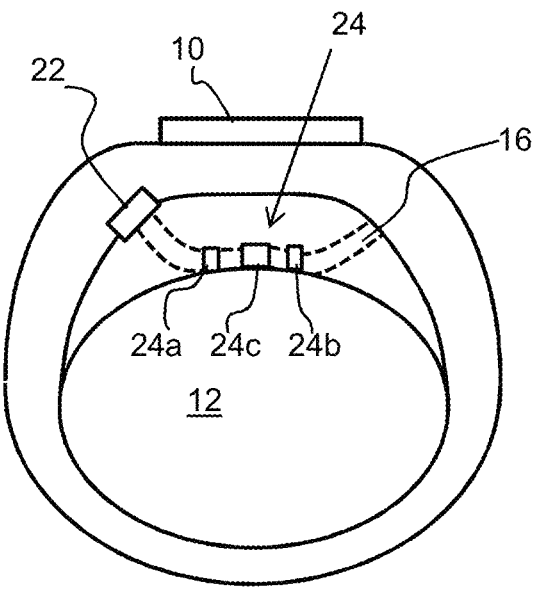
FIG. 2
FIG. 3
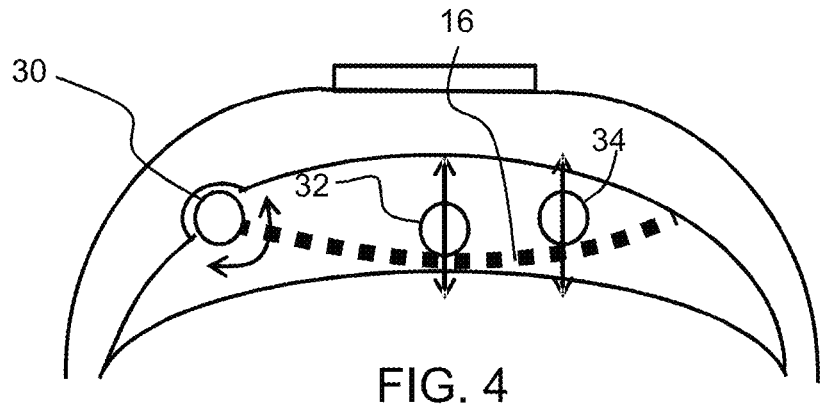
FIG. 4
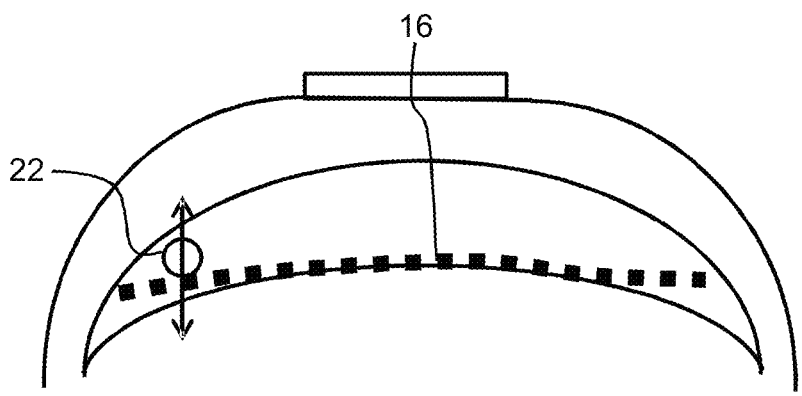
FIG. 5

APPARATUS FOR MEASURING A PHYSIOLOGICAL PARAMETER USING A WEARABLE SENSOR

FIELD OF THE INVENTION

This invention relates to sensors for measuring a physiological parameter of a subject, wherein the sensor can be worn by a user. Examples of wearable sensors include a photoplethysmographic (PPG) sensor, an electrocardiogram sensor, an ultrasound sensor, a heart rate sensor, and a skin monitoring sensor.

BACKGROUND OF THE INVENTION

It is becoming increasingly popular to monitor a physiological parameter of a subject using an apparatus including a wearable device. Such devices are convenient to use as they offer increased freedom of movement for the user whilst a physiological parameter is being monitored. In this way, it is possible to measure physiological parameters in a variety of circumstances, for example at different levels of physical exertion of the subject.

The physiological parameter sensor may be mounted to the user differently in different applications. The position of the mounted physiological parameter sensor relative to the subject may vary according to the parameter to be measured, the type of physiological parameter sensor, and/or the circumstances in which physiological sensing takes place.

In many cases, the physiological parameter sensor should be in contact with the user's body. One issue with respect to wearable sensors is ensuring that the contact between the physiological parameter sensor and the user's body is maintained and the contact pressure is maintained at a comfortable level.

One example of a sensor which has become particularly common is a wrist-worn heart rate monitor. This type of sensor enables a user to track some of their vital signals in a simple unobtrusive way. These sensors typically use either an optical PPG sensor which measures a blood volume pulse or else they use a bio-impedance sensor. Capacitive methods have also been investigated to sense heart rate.

PPG based sensors have the disadvantage that they have relatively high power consumption, as a result of the required LED. Thus, these sensors suffer from a short battery life.

Capacitive and bio-impedance based methods (as well as some PPG sensors) require good contact of the sensor with the skin. This may lead to skin irritation and wearing discomfort. One particular cause of discomfort is a sweat layer which forms between the sensor and the skin, because sweat is prevented from evaporating. Furthermore, this sweat layer may need to be retained to provide a desired galvanic contact. Some sensors are also susceptible to motion artifacts, making them inaccurate in cases of severe or particular motions of the subject.

More recently, heart rate and respiration rate sensors have been proposed using an accelerometer or gyroscope, which aims to measure subtle motions caused by arterial expansion and the beating of the heart. These may be described as motion-based methods. This approach is for example described in "Biowatch: Estimation of heart and breathing rates from wrist motions", J. Hernandez, D. McDuff, R. W. Picard, 9th International Conference on Pervasive Computing Technologies for Healthcare (PervasiveHealth) 2015, pp. 169-176.

A combination of sensor modalities may be used to improve the accuracy of results, for example using any combination of accelerometers, gyroscopes, and PPG sensors. The detection of individual blood pulses enables heart rate measurements, but also heart rate variability and heart rhythm measurements.

Motion sensing for sensing arterial (or other blood vessel) movements requires contact with the skin, which can give rise to discomfort, and the sensitivity needs to be high. There is therefore a need for a wearable device for measuring a physiological parameter that can provide accurate data and with reduced discomfort to the user.

SUMMARY OF THE INVENTION

The invention is defined by the claims.

According to examples in accordance with an aspect of the invention, there is provided a sensor apparatus for measuring a physiological parameter of a subject, wherein the sensor apparatus is adapted to be worn by the subject, comprising:

a housing;

a support structure carried by the housing, wherein the support structure has a contact portion which is adapted to be positioned by the housing against the skin of the subject, wherein at least the contact portion of the support structure is gas-permeable, wherein the support structure and the housing define an air space between the contact portion and the housing; and a motion sensor for sensing movement of the contact portion of the support structure, wherein the motion sensor is adapted to move relative to the housing.

This sensor design provides a gas-permeable (and in particular permeable for water vapor caused by sweating) support structure where contact is made with the subject. This breathable support structure reduces discomfort. An air space between the contact portion and the housing allows water vapor to escape so that an air flow may be present over the contact portion. The motion of the contact portion is detected, and this is decoupled from motion of the overall housing. For this purpose, the support structure is flexible.

In this way, the sensitivity is improved, in that motion being detected (e.g. an arterial pulse) only needs to impart kinetic energy to the support structure (with a relatively low inertia) and not to the housing. The motion sensor is thus no longer provided solidly in the housing of the complete apparatus.

The use of motion sensing enables a reduction in power consumption compared to a PPG-based wearable system. The invention gives improved accuracy for a motion sensing system while also reducing skin irritation and thus improving wearing comfort.

The housing for example comprises a band for wearing around the finger or wrist or a patch for wearing against the skin. A wrist band may be used to monitor arterial pulses in the wrist. A patch may be used over the heart to monitor pulse movement (local movements) but also chest movements (global movements of the housing).

The band may comprises different elements, such as a rigid housing part and a flexible strap part. The flexible strap part is preferably adjustable so that the device can fit different users.

The support structure for example comprises a plate which is mounted at opposite edge portions to the housing with the contact portion biased towards the subject. This bias maintains contact with the subject so that movements of the skin are translated into movements of the contact portion, which can then be sensed by the motion sensor.

The motion sensor is for example attached to the support structure. It may be attached to:
- an edge portion of the support structure;
- the contact portion; or
- an intermediate portion between the contact portion and an edge portion.

When mounted at an edge portion, the motion sensor may detect a pivoting movement rather than a linear movement, in that movement of the contact portion results in a pivoting movement at the edge portions.

The motion sensor for example comprises an accelerometer and/or gyroscope. There may be one motion sensor or a plurality of motion sensors. The use of multiple sensors can enable more accurate measurements, for example enabling more accurate signal filtering in order to isolate the local movements of the contact portion.

The support structure may have one of a number of designs, such as:
- a non-conducting mesh; or
- a supporting mesh and a non-conducting coating; or
- a conducting supporting mesh and a non-conducting coating, wherein electrical connections to the motion sensor are made using the conducting supporting mesh.

The mesh (and coating if there is one) may be supported within an outer frame.

In one example, the support structure comprises a perforated nylon mesh supported within an outer frame.

In all cases, the mesh openings provide the desired permeability. The perforations may be at macro scale (i.e. holes within a non-permeable layer) or at the micro scale (i.e. a material which is inherently permeable).

One or more additional sensors may be carried by the support structure or the housing. This makes the sensor system more robust, in that different sensor modalities may be used.

The one or more additional sensors for example comprise one or more of a PPG sensor, a capacitive sensor or a bio-impedance sensor.

The apparatus preferably further comprises a controller which is adapted to activate one or more of the additional sensors in dependence on a signal quality associated with the motion sensor.

In this way, the motion sensing modality may be used to achieve low power consumption. If the signal quality drops below a threshold, other sensing modalities may be used as well or instead, to maintain reliable sensor readings, although at the expense of temporarily increased power consumption.

The controller may be adapted to combine signals from multiple sensors with weighting factors to derive a combined sensor signal. This enables a reliable sensor signal to be provided which makes best use of the different sensor modalities.

The controller may be adapted to provide an alert to the subject that sensor contact has been lost in dependence on the signal characteristics of the motion sensor. This alert may for example be used to advise the subject that they need to tighten the housing strap or reapply the housing patch (as the case may be).

The apparatus is for example for measuring heart rate and/or respiration rate and/or heart rate variability and/or heart rhythm.

BRIEF DESCRIPTION OF THE DRAWINGS

Examples of the invention will now be described in detail with reference to the accompanying drawings, in which:

FIG. 2 shows a first example of a wearable sensor;
FIG. 3 shows a second example of a wearable sensor;
FIG. 4 shows different possible motion sensor locations;
FIG. 5 shows a third example of a wearable sensor.

DETAILED DESCRIPTION OF THE EMBODIMENTS

The invention provides a wearable physiological sensor which has a housing and a gas-permeable support structure carried by the housing, which contacts the skin of the subject. An air space is provided between the support structure and the housing. Movement of the support structure relative to the housing is sensed. This provides a sensor which is comfortable for the subject and provides good sensitivity in that motion being detected (e.g. an arterial pulse) only needs to impart kinetic energy to the support structure, with a relatively low inertia.

Figure 1:
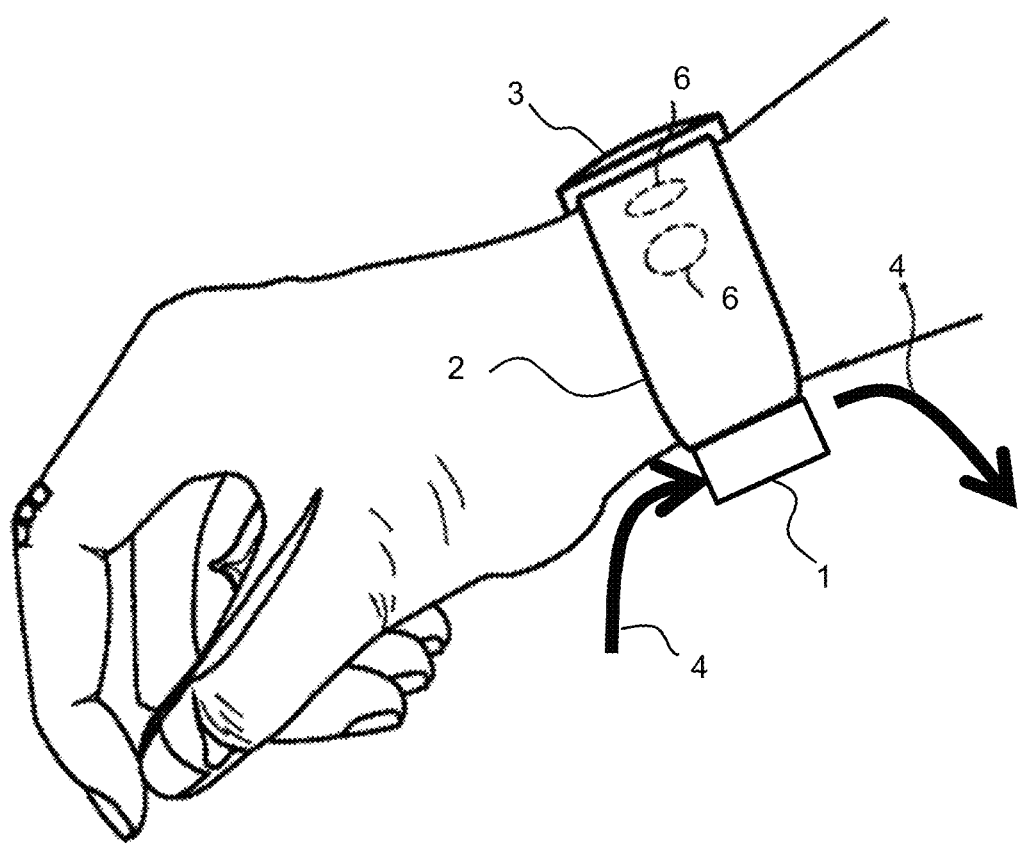
FIG. 1 shows a wrist-worn sensor and shows the concept underlying the invention.

FIG. 1 shows a wrist-mounted sensor comprising a sensor part 1 and a wrist strap 2. The sensor part 1 includes a motion sensor, such as an accelerometer for sensing local movements caused by the artery. In the example shown, it is provided under the wrist. An output unit 3 is provided on top of the wrist. The output unit 3 may combine all normal wrist watch or smart watch functions, together with the sensor output display function.

The sensor part 1 is designed to allow air flow across the sensor area as shown by arrows 4. This air flow increases user comfort. For this purpose, the sensor part 1 The strap 2 may also be porous as shown schematically by the openings 6. The overall device forms a band, in this example to be worn around the wrist.

FIG. 2 shows an example of the sensor apparatus in more detail. The sensor apparatus is for measuring a physiological parameter of a subject. This example again comprises a wrist band, placed around the wrist 12 of the subject. For simplicity only the sensor part is shown in detail, with an output device shown schematically as 10. In this example, the sensor part is for positioning on top of the wrist. Thus, FIGS. 1 and 2 show that for a wrist mounted device, the sensor part may be on top or underneath the wrist, and there may be a read out part (similar to a watch face) at the same or a different location to the sensor part.

The sensor apparatus comprises a housing 14 and a flexible support structure 16 carried by the housing. The support structure has a contact portion 18 which contacts the skin of the user. The contact portion 18 is urged against the skin in use. This results from the design of the support structure 16 and the housing 14.

For example, the support structure 16 may be a non-planar plate which has a bias towards the subject. By this is meant that the natural shape of the support structure is such that the contact portion 18 presses against the wrist. It may have a bowed shape as shown. When the sensor is attached to the wrist to a suitable tightness, the contact portion is pressed against the skin.

Alternatively, the support structure may be planar, such as a flat stretched mesh, which extends within a plane which in use is intersected by the skin of the subject. The aim is to maintain contact between the contact portion 18 and the subject when the sensor arrangement is worn.

At least the contact portion 18 of the support structure is gas-permeable and in particular for water vapor. This may be achieved by forming the support structure 16 as an open mesh or grid structure or as a solid layer with an array of openings. The support structure 16 may have a single design or it may have a different design for the contact portion compared to the other parts of the support structure which attach the contact portion to the housing 14. It has some flexibility, and may be sprung to be biased into a particular shape.

An air space 20 is provided between the contact portion 18 and the housing 14. This means that sweat formed at the contact portion 18 is able to penetrate through the support structure, and is then vented to the ambient surroundings.

A motion sensor 22 is provided for sensing movement of the contact portion 18 of the support structure. The motion sensor (in particular the part of the motion sensor which moves) is able to move relative to the housing 14. It is formed within and therefore protected by the housing 14. It comprises an accelerator or a gyroscope or a combination of multiple accelerometers and/or multiple gyroscopes.

The motion sensor 22 may be mounted at the contact portion 18 itself, so that the motion to be detected (e.g. arterial pulses at the location of the contact portion) is detected directly. However, the motion sensor may be remote from the contact portion. In this case, the support structure acts as a motion transferal mechanism from the contact portion to the motion sensor. The motion is imparted to the support structure at the contact portion, and this motion is sensed at another location of the support structure.

FIG. 2 for example shows the motion sensor at an edge portion of the support structure 16. In that position it detects the angular motion resulting from a change in the position of the contact portion, rather than detecting the translational movement of the contact portion 18 directly.

For angular motion detection, there is a direct relationship between the linear translation at the contact portion and the angle made between the contact portion and the housing. The detected angle can thus be converted into a level of translational movement.

For direct translational motion detection, the function of displacement with respect to time provides a direct measure of the pulse pressure as a function of time.

Slowly varying movements (outside the frequency range of interest) as detected by the motion sensor can be filtered out from the motion signals so that only arterial pulse motions are processed.

The detected motion (i.e. arterial movements) is transferred to the support structure 16 but not to the housing 14. For example, the motion sensor may be attached to the support structure only. This improves the sensing accuracy since the inertia of the part which is directly coupled mechanically to the subject is reduced.

Electrical connection may be made to the motion sensor by wires which do not impede the movement. However, an alternative option is for the support structure 16 to include conductor lines, for example formed as a conducting mesh.

This sensor design uses a gas-permeable support structure to reduce discomfort. The air space 20 allows sweat to escape. The motion sensor has low power consumption compared to a PPG-based wearable system.

The support structure may have multiple parts, such as a mesh and a coating. The mesh may provide the required mechanical and/or electrical properties of the support structure and the coating may provide the desired skin contact properties. A single layer mesh may instead be used.

The support structure 16 is for example formed as a conductive mesh for example with a biocompatible coating. It may have a total thickness in the range 0.5 mm to 2 mm.

The mesh has a sufficient rigidity to remain in contact with the skin, but sufficient flexibility to react to arterial movements. The rigidity of the support structure may be an inherent property of the material used, or else a less rigid material may be provided within a frame which holds the material taught.

The conductive mesh part may be used to convey electrical signals from the motion sensor and to provide power to the motion sensor from an on-board battery.

The material of the support structure should be sufficiently strong for durability and hence there is a limit on how thin it can be. The outer material will be biocompatible. The support structure may extend across nearly the full width of the band (by which is meant the strap width direction, i.e. left-right in FIG. 1). The height of the air gap 20 is for example in the range from 0.5 mm to a few mm.

The support structure may make contact with the skin only at a local contact portion, or else a larger contact area may be provided. There may be one large support structure mesh, or multiple smaller support structure meshes.

The support structure for example comprises a nylon mesh supported within a perimeter frame. An alternative is a rubber mesh or any other breathable material suspended in a frame. The mesh supported within the frame may include conductor lines or a conducting mesh as explained above, for providing electrical connection to the motion sensor.

The housing 14 may also be gas permeable where it contacts the skin, for example the strap region 23. The wrist strap is for example made of a sweat absorbing or sweat permeable material, or has microscopic and/or macroscopic openings to allow sweat to escape.

FIG. 2 shows a device worn around the wrist. It may instead be designed for wearing around the finger as a ring, or clipped on a fingertip or clipped over an earlobe.

FIG. 3 shows a modification in which additional sensors are provided within the housing, mounted on the support structure 16. FIG. 2 shows a PPG sensor 24 mounted at the contact portion 18, comprising two LEDs 24a, 24b and a photodiode sensor 24c. The PPG sensor provides an alternative pulse detection mechanism.

The PPG sensor components may be mounted on the support structure as shown. The LEDs and photodiode shown in FIG. 2 may instead be mounted on the inside of the housing. The LED light may the pass through the holes of the support structure 16 and will be received by the photodiode accordingly, or the material of the support structure may be transparent for the wavelength of the LED light. This has as advantage that the construction can be made more robust, and less heat will be dissipated by the skin due to the photodiode and LEDs.

Other sensors may also be included for pulse detection, such as capacitive, and/or bio-impedance sensors. The system can then use a combination of sensor readings to improve the accuracy.

FIG. 4 shows three possible locations for the motion sensor 22. As explained above, one option is to provide the motion sensor at an edge portion of the support structure 16 in order to detect angular movement. This has the advantage that the overall sensor package is mounted to the housing 14 making the overall design robust. This is shown as location 30. Another option is at the contact portion 18 shown as location 32. Another option is at an intermediate location between the center contact portion of the support structure and the edge. In this way, the sensor does not block the permeable support structure at the contact portion, but it may still be used for detecting linear translational displacement.

In all cases, the sensor itself, or else a sensing portion of the sensor, can move with respect to the housing 14. The sensor may communicate its sensing signals over wires within the apparatus to a signal processing unit within the housing, or wirelessly to that signal processing unit or to a remote signal processing unit.

There may be multiple motion sensors at different locations. This may be used to make the pulse detection more sensitive, and the motion sensors can also be used to correct for motion artifacts appearing in other additional sensor signals, for example in a PPG or capacitive or bio-impedance-based sensor.

The motion sensor shown in FIGS. 1 to 3 may be at the top of the wrist (at the side where the display of the watch would be) instead of on the opposite side of the wrist as shown in FIG. 1.

FIG. 5 shows that the support structure 16 may be in the form of a flat stretched netting. The support structure then does not need to be a curved structure, but the position in which the support structure 16 is mounted provides the required contact when the apparatus is worn. Thus, the netting is deformed to follow the shape of the wrist when the device is worn. The netting has some resistance to bending so that the contact portion is then urged against the skin. However, the netting is sufficiently flexible that it does not suppress arterial movement and motion sensing at the contact portion or remote from the contact portion may again be employed.

The examples above are based on a band-type device, for example worn around the wrist or finger.

Figure 6:
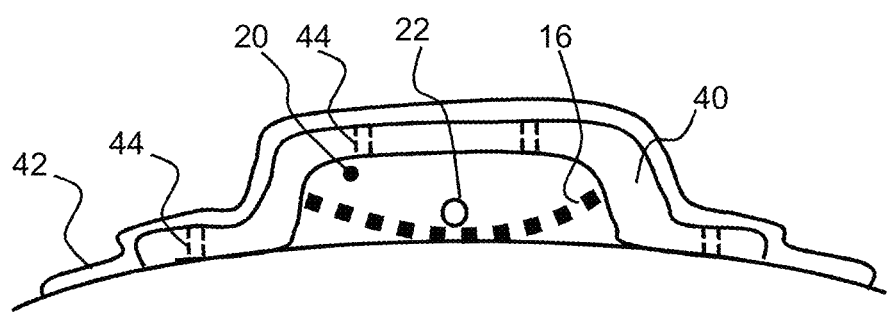
FIG. 6 shows a fourth example of a wearable sensor.

FIG. 6 shows a patch design.

The apparatus has a rigid housing 40 which mounts the support structure 16 and motion sensor 22, which all function exactly as described above. The housing 40 is attached to the skin by an adhesive patch 42. The air space 20 is vented to the outside. This may be achieved in a number of different ways. One option is to provide a patch 42 only at the sides, leaving an open air flow channel to the space 20. Another option is to provide openings 44 in the housing 40 in combination with a gas-permeable patch 42. Thus, the whole structure is able to breath and the air space 20 may then be physically closed (on a more macroscopic level).

The patch design can be applied to the chest over the heart. In this way, a seismocardiogram may be obtained based on the motion sensor measuring the direct beating of the heart. The sensitivity may be sufficient to measure the individual cycles of the heartbeat. By incorporating a PPG sensor as well, the pulse transit time (PTT) could also be determined from the time difference between the (first) beat in the motion sensor signal and the pulse measured in the PPG signal.

The heart beat is detected based on local motion sensing. More global motion sensing may be used to determine a respiration rate, functioning as a chest belt.

The apparatus may further include ECG electrodes, and in this case a pre-ejection period (PEP) could be derived.

Figure 7:
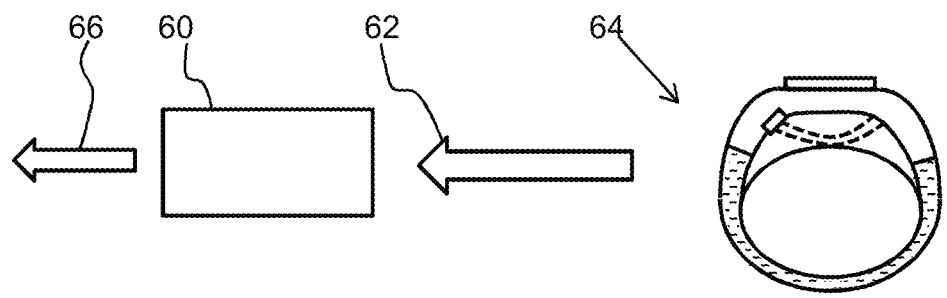
FIG. 7 shows a sensor system.

FIG. 7 shows the overall system, in which a controller 60 receives the sensor signals 62 from the sensor hardware 64 and generates an output signal 66.

The controller 60 may be within the housing of the device, and the device may then include an output device such as a display. Thus, the system may be fully self-contained, for example in the form of a wrist band device. The controller 60 may instead be remote with wireless or wired communication from the sensor hardware 64 to the controller 60.

The controller 60 can perform various signal processing functions to improve the accuracy of the measurements and/or to minimize power consumption, and some of these approaches are discussed below.

A first approach relates to the selection of which sensor modalities to use at any given time, when there are multiple sensor types. If the signal to noise ratio of the motion sensor based pulse detection is high, for example because there are low movement artifacts, the other sensing modalities (PPG or capacitive or bio-impedance) may then be switched off to save power. The output 66 is then derived from the motion sensor system only, which is a modality that is very low in power consumption. The other sensor modalities may be switched on as soon as the motion sensor system produces unreliable signals. Thus, additional sensors may be used when greater accuracy is desired.

Another indication of low quality signals may be when the pulse detection by one of the modalities (e.g. the motion-sensor based modality) differs from that of another modality (e.g. the PPG based modality).

In this way, one or more of the additional sensors may be activated in dependence on a signal quality associated with the motion sensor. The additional sensors may instead be operated periodically to make other measurements less frequently.

A second approach relates to use of the motion sensing to provide verification of the function of the other sensors. Accelerometer signals may for example be used to check if an optical sensor (e.g. PPG sensor) makes contact with the skin. If not, the user may be advised to tighten the band or reapply the patch.

In this way, an alert may be provided to the subject that sensor contact has been lost in dependence on the signal characteristics of the motion sensor. In particular, no local acceleration signals (i.e. no detected pulse signal) may be an indication that sensor contact has been broken.

A third approach relates to the combination of multiple sensor signals. An optical sensor system is sensitive to blood volume changes of the surface layers of skin, while the motion sensor system is sensitive to blood volume changes deep in the tissue.

The ratio of the two is indicative of the structure and response of the blood vessels. In addition, an average heart rate may be calculated as:

$$w*M1+(1-w)*M2.$$

Here w is a weighting factor which may be determined based on the reliability of the first modality M1 (i.e. motion based), and the second modality M2 e.g. PPG, bio-impedance, or capacitive based. The reliability of M1 or M2 may be based on the level of distortion in the signals, in order to determine the weighting factor w.

When PPG-sensing is turned on, distortion of the signal by ambient light may be compensated by known techniques, such as using a duty cycle in which the LEDs are turned on and turned off and where the signal in the off-state is subtracted from the signal in the on-state. Angle selective filtering in front of the PPG photodetector or wavelength selective filtering may also be used (e.g. an infrared-blocking filter).

The invention is of primary interest for a wearable device for pulse detection to derive one or more of heart rate, heart rate variability and heart rhythm (e.g. detection of atrial fibrillation). Respiration rate may also be obtained. Such a wearable device can be used in a general hospital ward or at home.

As mentioned above, the main physiological parameter of interest is the heart rate, or parameters related to the heart rate. Other possible measurements include the blood oxygen saturation (SpO2) using an SpO2 sensor, ECG measurements using ECG an electrodes in contact with the skin, and ultrasound measurements using an ultrasound transducer.

As discussed above, embodiments make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Other variations to the disclosed examples can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A sensor apparatus configured for measuring a physiological parameter of a subject, comprising:
a housing adapted to be worn by the subject;
a support structure coupled to and carried by the housing in a location configured between an inside of the housing and skin of the subject when worn, wherein the support structure comprises a flexible structure that includes a contact portion which is adapted to be positioned and biased, via the housing, against the skin of the subject, wherein only the flexible structure that includes the contact portion is configured to receive kinetic energy imparted by a motion of the skin and not the housing, wherein at least the contact portion of the support structure is gas-permeable, and wherein the support structure and the housing define an air space between the contact portion and the inside of the housing, the air space further being configured for overlying the contact portion and the skin of the subject;
a motion sensor coupled to the support structure for sensing movement of the contact portion of the support structure, wherein the motion sensor is adapted to move relative to the housing, wherein the support structure further comprises a conducting supporting mesh and a non-conducting coating, wherein electrical connections to the motion sensor are made using the conducting supporting mesh;
one or more additional sensors carried by the support structure or the housing, wherein the one or more additional sensors comprise one or more of a photoplethysmographic (PPG) sensor, a capacitive sensor or a bio-impedance sensor; and
a controller adapted to activate (i) the motion sensor in a motion sensor-based modality and (ii) the one or more of the additional sensors in an additional sensor-based modality, wherein the controller is adapted to switch off the one or more of the additional sensors in the additional sensor-based modality in response to (SNR) of the motion sensor-based modality being above a given threshold SNR and thereby measure the physiological parameter of the subject using only the motion sensor-based modality to minimize a power consumption for measuring the physiological parameter, and wherein the controller is adapted to switch on the one or more of the additional sensors in the additional sensor-based modality in response to the signal to noise ratio of the motion sensor-based modality being below the given threshold SNR and thereby measure the physiological parameter of the subject using at least the additional sensor-based modality to improve a measurement accuracy of the physiological parameter.

2. The sensor apparatus as claimed in claim 1, wherein the housing comprises a band configured for wearing around the finger or wrist or a patch configured for wearing against the skin.

3. The sensor apparatus as claimed in claim 1, wherein the support structure comprises a plate which is mounted at opposite edge portions to the housing with the contact portion configured for and positioned to make contact with the skin of the subject.

4. The sensor apparatus as claimed in claim 3, wherein the motion sensor is attached to the support structure.

5. The sensor apparatus as claimed in claim 4, wherein the motion sensor is attached to:
an edge portion of the support structure;
the contact portion; or
an intermediate portion of the support structure between the contact portion and an edge portion.

6. The sensor apparatus as claimed in claim 1, wherein the support structure comprises the conducting supporting mesh supported within an outer frame.

7. The sensor apparatus as claimed in claim 1, wherein the motion sensor comprises an accelerometer and/or gyroscope.

8. The sensor apparatus as claimed in claim 1, comprising a plurality of motion sensors.

9. The sensor apparatus as claimed in claim 1, further wherein the controller is further adapted to activate the one or more additional sensors in dependence on a given signal quality associated with the motion sensor.

10. The sensor apparatus as claimed in claim 1, further wherein the controller is further adapted to combine signals from multiple sensors with weighting factors to derive a combined sensor signal.

11. The sensor apparatus as claimed in claim 1, further wherein the controller is further adapted to provide an alert to the subject that sensor contact has been lost in dependence on signal characteristics of the motion sensor.

12. The sensor apparatus as claimed in claim 1, wherein the physiological parameter comprises one or more of heart rate and/or respiration rate and/or heart rate variability and/or heart rhythm.

* * * * *